United States Patent [19]

Umemura et al.

[11] 4,165,341

[45] Aug. 21, 1979

[54] PROCESS FOR PREPARING PROTOCATECHUALDEHYDE AND ITS DERIVATIVES

[75] Inventors: Sumio Umemura; Nagaaki Takamitsu; Takuji Enomiya; Hiroshi Shiraishi; Takato Nakamura, all of Ube, Japan

[73] Assignee: Ube Industries, Ltd., Ube, Japan

[21] Appl. No.: 869,608

[22] Filed: Jan. 16, 1978

[30] Foreign Application Priority Data

Feb. 4, 1977 [JP] Japan .................................. 52/10733
May 10, 1977 [JP] Japan .................................. 52/52590

[51] Int. Cl.$^2$ ............................................. C07C 45/18
[52] U.S. Cl. ............................ 260/600 R; 260/600 A; 562/470
[58] Field of Search ...................... 260/600 R, 600 A; 562/478, 470

[56] References Cited

U.S. PATENT DOCUMENTS 2,062,205  11/1936  Boedecker ......................... 260/600
2,199,748  5/1940   Mather et al. ..................... 260/600

FOREIGN PATENT DOCUMENTS 37-4122   6/1962  Japan .................................. 260/600 R
50-78137  3/1975  Japan .................................. 260/600 R Primary Examiner—Bernard Helfin
Attorney, Agent, or Firm—Flynn & Frishauf

[57] ABSTRACT

A process for preparing protocatechualdehyde or a 3-alkoxy-4-hydroxybenzaldehyde which comprises subjecting catechol or a 2-alkoxyphenol to reaction with glyoxylic acid in a basic aqueous medium in the presence of a catalyst containing one or more compounds selected from aluminium oxide, silicon oxide and hydrated aluminium oxide in an amount of not less than 0.01 g per 1 g of the starting catechol or 2-alkoxyphenol at a temperature of 0° to 50° C., and then oxidizing the thus obtained reaction mixture in a basic medium.

8 Claims, No Drawings

PROCESS FOR PREPARING PROTOCATECHUALDEHYDE AND ITS DERIVATIVES

This invention relates to a process for preparing protocatechualdehyde, or a 3-alkoxy-4-hydroxybenzaldehyde.

It has heretofore been known publicly that protocatechualdehyde can be prepared by the oxidation of the reaction mixture which is obtained by the reaction of catechol with glyoxylic acid in a basic aqueous medium (Japanese Patent Publication No. Sho 37-4122/1962).

According to the method described in the above-mentioned publication, the conversion of catechol is 62.4% and the selectivity to protocatechualdehyde is around 70% based on the catechol consumed (see Comparative example 1).

It has also been known publicly that 3-methoxy-4-hydroxybenzaldehyde can be prepared by the oxidation of the reaction mixture obtained by the reaction of 2-methoxyphenol with glyoxylic acid in a basic aqueous medium. According to the process, the yield of 4-hydroxy-3-methoxybenzaldehyde is 80–83% based on 2-methoxyphenol consumed, and 2-hydroxy-3-methoxybenzaldehyde and 4-hydroxy-5-methoxyisophthalaldehyde are formed as by-products in yields of 3–4% and 10–15%, respectively based on the 2-methoxyphenol consumed (see Comparative example 3).

Therefore, the known processes are not advantageous for preparing protocatechualdehyde and 4-hydroxy-3-methoxybenzaldehyde.

This invention provides a process for preparing protocatechualdehyde, or a 3-alkoxy-4-hydroxybenzaldehyde in higher yields and selectivities than the prior processes.

Namely, this invention is a process for preparing protocatechualdehyde or a 3-alkoxy-4-hydroxybenzaldehyde represented by the formula

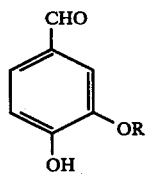

wherein R represents a methyl group or an ethyl group, which comprises subjecting catechol or a 2-alkoxyphenol represented by the formula

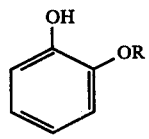

wherein R has the same meanings as defined above, to reaction with glyoxylic acid in a basic aqueous medium in the presence of a catalyst containing one or more compounds selected from aluminium oxide, silicon oxide and hydrated aluminium oxide in an amount of not less than 0.01 g per 1 g of the starting catechol or 2-alkoxyphenol at a temperature of 0° to 50° C., and then oxidizing the thus obtained reaction mixture in a basic aqueous medium.

Next, the reaction steps of this invention will be explained below.

[The first step: Reaction of catechol or a 2-alkoxyphenol with glyoxylic acid]

In the process of this invention, catechol or a 2-alkoxyphenol and glyoxylic acid are used as the starting materials. As the 2-alkoxyphenol, 2-methoxyphenol or 2-ethoxyphenol is used. Glyoxylic acid may be used as it is or in the form of a sodium or potassium salt.

The amount of glyoxylic acid to be used is not limited in particular, but it usually is within a range of 0.5–2 moles, preferably, 0.5–1.0 mole per 1 mole of catechol or a 2-alkoxyphenol.

The reaction is carried out in the presence of a catalyst containing one or more compounds selected from aluminium oxide, silicon oxide and hydrated aluminium oxide. As the catalyst, there may be exemplified silicon dioxide, aluminium oxide ($Al_2O_3$), aluminium oxide monohydrate such as boehmite and diaspore, and aluminium oxide trihydrate such as gibbsite and bayerite. As the aluminium oxide, there may be employed $\alpha$, $\gamma$, $\delta$, $\theta$, $\eta$ and $\chi$ types thereof and so on. Further, a silica-alumina, a diatomaceous earth containing silicon dioxide as a main component and an active-clay containing aluminium oxide and silicon dioxide as main components may be included in the catalysts of this invention. Among these catalyst, aluminium oxide and hydrated aluminium oxide may preferably be used on the standpoints of the conversion of catachol or a 2-alkoxyphenol and the selectivity to protocatechualdehyde or a 3-alkoxy-4-hydroxybenzaldehyde.

The amount of the catalyst to be used is not less than 0.01 g, preferably not less than 0.05 g per 1 g of catechol or the 2-alkoxyphenol. When the amount of the catalyst to be used is below the lower limit, the yield of protocatechualdehyde or a 3-alkoxy-4-hydroxybenzaldehyde is decreased. As to the upper limit in the amount of the catalyst to be used, there is no limitation in particular. But, even if it is used in excess amounts, the desired product can not be obtained in higher yields and more time is required for removing the catalyst after reaction. So, there is usually used not more than 1.5 g of the catalyst per 1 g of catechol or a 2-alkoxyphenol.

The reaction is carried out in a basic aqueous medium in which a basic compound such as sodium hydroxide, potassium hydroxide and sodium carbonate is dissolved. The reaction can substantially not proceed in a neutral or acidic aqueous medium.

The amount of water to be used is not limited in particular, but it usually is 0.5–1.5 l per 1 mole of catechol or a 2-alkoxyphenol.

The reaction may be carried out in accordance with the following methods.

(1) The reactants dissolved in a basic aqueous medium are brought into contact with the catalyst suspended in the medium.

(2) The reactants dissolved in a basic aqueous medium are brought into contact with a fixed bed of the catalyst.

The reaction temperature is 0°–50° C., preferably 10°–40° C. When the reaction temperature is below 0° C., the rate of reaction becomes undesirably low and when it is above 50° C., glyoxylic acid is undesirably converted by Cannizzaro's reaction into oxalic acid and glycolic acid.

As to reaction time, there is no limitation in particular, but it usually is 0.5–40 hours.

When a fixed bed of the catalyst is used, the basic aqueous medium containing the reactants may preferably be recycled through the bed to effect the reaction sufficiently.

The reaction mixture obtained in the first step may be used as such for the second step without further purification. However, in the case of industrial practices, it is preferable to recover an unaltered catechol or 2-alkoxyphenol from the reaction mixture obtained in the first step after removal of the catalyst.

The unaltered catechol or 2-alkoxyphenol may be recovered, for example, by the following method. Namely, a mineral acid such as hydrochloric acid, sulfuric acid, etc., is added to the aqueous solution, which was obtained by removing the catalyst from the reaction mixture, to adjust the pH value to 5-7 and then the unaltered catechol or 2-alkoxyphenol is extracted with an organic solvent such as ether, benzene, toluene, etc. When the pH value of the aqueous solution is above 7, the unaltered catechol or 2-alkoxyphenol is insufficiently extracted and when it is below 5, the reaction product is undesirably extracted along with the unaltered catechol or 2-alkoxyphenol.

After extraction, the organic layer is separated from the aqueous layer and then catechol or a 2-alkoxyphenol is recovered from the separated organic layer by a known method, for example, by distillation. The aqueous layer is provided as the starting material for the second step. The catalyst removed from the reaction mixture may be recycled and reused.

[The second step: Oxidation of the product obtained in the first step]

In the second step, the reaction mixture obtained in the first step, the mixture obtained by removing the catalyst from the reaction mixture or the aqueous layer obtained from the reaction mixture by separating the unaltered catechol or 2-alkoxyphenol and the catalyst according to the above-mentioned method (hereinafter referred to as "aqueous layer" in short) is subjected to oxidation in a basic aqueous medium.

In an acidic or neutral medium, the rate of reaction is low so that the process becomes impractical.

When catechol is used as a starting material in the first step, the oxidation is preferably carried out at a pH value of 9.5-11.5, more preferably 9.7-11.3.

In cases where the reaction mixture obtained in the first step is used as a starting material in the second step, it may be subjected as such to oxidation since it is basic.

In cases where the aqueous layer obtained from the reaction mixture by removing the unaltered catechol or 2-alkoxyphenol is used as a starting material, it is required to make the aqueous layer basic by adding thereto such a basic substance as sodium hydroxide, potassium hydroxide, sodium carbonate, etc.

As the oxidation method, there may be mentioned the followings.

(1) Oxidation of the reaction mixture or the aqueous layer with oxide of a metal such as copper, iron, cobalt, manganese, chromium, mercury, platinum, aluminium, silver, vanadium, nickel, etc.

(2) Oxidation of the reaction mixture or the aqueous layer by blowing an oxygen-containing gas thereinto.

(3) Oxidation of the reaction mixture or the aqueous layer by blowing an oxygen-containing gas thereinto in the presence of the metal oxide mentioned above.

Among these methods, method (1) is preferable when catechol is used as a starting material in the first step. When a 2-alkoxyphenol is used as a starting material in the first step, method (2) or (3) is preferable. As the metal oxide in method (1), there may preferably be used copper (II) oxide, zinc oxide, manganese (II) oxide, manganese (IV) oxide and manganese (VI) oxide. The amount of the metal oxide to be used is 3-15 moles, preferably 5-10 moles per 1 mole of the catechol or 2-alkoxyphenol consumed in the first step.

In cases where aluminium oxide was used as the catalyst in the first step, there may be adopted a process in which oxidation is conducted by blowing oxygen gas or an air directly into the reaction mixture obtained in the first step since the oxide also catalyzes the oxidation in the second step.

As to the reaction temperature, there is no limitation in particular, but is usually is in a range of 80°-150° C., preferably 90°-125° C.

The oxidation reaction may be conducted under atmospheric pressure or under pressure.

The reaction time for oxidation is not limited in particular, but it usually is 0.5-3.0 hours.

The desired product of this invention can be isolated from the reaction mixture, for example, by the following method.

To the oxidation reaction mixture is added such a mineral acid as hydrochloric acid, sulfuric acid, etc., until the pH value becomes below 7, preferably below 5. Then, protocatechualdehyde or a 3-alkoxy-4-hydroxybenzaldehyde, namely, the desired product of this invention is extracted from the reaction mixture along with the by-products such as 2,3-dihydroxybenzaldehyde and 4,5-dihydroxyisophthalaldehyde, or 3-alkoxy-2-hydroxybenzaldehyde and 5-alkoxy-4-hydroxyisophthalaldehyde by using such an organic solvent as ether, benzene, toluene, xylene, etc. Thereafter, the organic solvent layer separated from an aqueous layer is distilled to evaporate the organic solvent, and then 2,3-dihydroxybenzaldehyde or a 3-alkoxy-2-hydroxybenzaldehyde. The distillation is continued further to evaporate and isolate protocatechualdehyde or a 3-alkoxy-4-hydroxybenzaldehyde.

According to the present invention the selectivity to protocatechualdehyde or a 3-alkoxy-4-hydroxybenzaldehyde is higher than that in publicly known methods and the conversion of catechol or a 2-alkoxyphenol is not reduced as compared with the prior methods. Further, not only the selectivity to protocatechualdehyde but also the conversion of catechol are higher than those in conventional methods, when aluminium oxide or hydrated aluminium oxide is used as the catalyst in the first step of the present invention.

Protocatechualdehyde and a 3-alkoxy-4-hydroxybenzaldehyde obtained according to this invention are useful as an intermediate for perfumes or pharmacenticals, and a perfume itself, respectively.

Next, Examples and Comparative examples are shown below. In the Examples and Comparative examples, the analyses of the products are conducted by gas chromatography.

EXAMPLE 1

To 45 ml of a 2 N aqueous solution of sodium hydroxide were added 5.50 g of catechol, 14.25 g of a 20 wt % aqueous solution of glyoxylic acid and 2.50 g of aluminium oxide [manufactured by Kishida Chem. Co., Ltd., trade name: Kassei Alumina], and the mixture was subjected to reaction with stirring at 25° C. for 24 hours.

The aluminium oxide was separated from the reaction mixture by filtration and thus a reaction liquid was obtained. The aluminium oxide separated by filtration was washed with 20 ml of a 1 N aqueous solution of sodium hydroxide and the washing was added to the reaction liquid. The reaction liquid was adjusted to pH 6 by the addition of a 12 N hydrochloric acid and then the unaltered catechol was extracted three times with 50 ml portions of diethyl ether. From the extract was recovered 1.61 g of catechol.

After nitrogen gas was blown into the aqueous layer obtained after extraction to remove the dissolved oxygen, 33 g of sodium carbonate was added thereto to adjust the pH value to 10.5. Further, 20 g of a powdery copper (II) oxide was added thereto, and the mixture was placed into an autoclave and subjected to reaction at 98° C. for 50 minutes with stirring while the pressure was allowed to rise. The pH value of the reaction liquid after reaction was 10.0.

After cooling the reaction mixture, the copper oxide was separated by filtration. To the thus obtained reaction liquid was added a 12 N hydrochloric acid to adjust the pH value to 2. Organic substances in the solution were extracted six times with 150 ml portions of diethyl ether.

Protocatechualdehyde in the extract was determined by gas chromatography.

The conversion of catechol was 70.7%, the yield of protocatechualdehyde was 4.51 g and the selectivity (based on the catechol consumed in the first step; this meaning is applied similarly to the following examples) was 92.4%.

COMPARATIVE EXAMPLE 1

An experiment was run in the same manner as in Example 1 except that aluminium oxide was not used.

After the first step, 2.07 g of catechol was recovered. The conversion of catechol was 62.4%, the yield of protocatechualdehyde was 3.06 g and the selectivity was 71.1%.

EXAMPLES 2–4

Experiments were run in the same manner as in Example 1 except that 0.10 g (Example 2), 0.55 g (Example 3) or 5.50 g (Example 4) of aluminium oxide was used.

The amounts of catechol recovered after the first step, the conversions of catechol, the yields of protocatechualdehyde and the selectivities are shown in Table 1.

COMPARATIVE EXAMPLE 2

An experiment was run in the same manner as in Example 1 except that 0.02 g of aluminium oxide was used.

The results are shown in Table 1.

Table 1

| | catechol | | protocatechualdehyde | |
|---|---|---|---|---|
| | recovery (g) | conversion (%) | yield (g) | selectivity (%) |
| Example 2 | 2.01 | 63.5 | 3.60 | 82.2 |
| Example 3 | 1.89 | 65.6 | 4.01 | 88.6 |
| Example 4 | 1.60 | 70.9 | 4.52 | 92.4 |
| Comparative example 2 | 2.05 | 62.7 | 3.10 | 71.6 |

EXAMPLES 5–10

Experiments were run in the same manner as in Example 1 except that each 3.00 g of respective catalysts described in Table 2 was used.

The results are shown in Table 2.

Table 2

| | | catechol | | protocatechualdehyde | |
|---|---|---|---|---|---|
| Ex. | catalyst | recovery (g) | conversion (%) | yield (g) | selectivity (%) |
| 5 | boehmite | 1.68 | 69.5 | 4.33 | 90.3 |
| 6 | diaspore | 1.65 | 70.0 | 4.38 | 90.7 |
| 7 | gibbsite | 1.70 | 69.0 | 4.30 | 90.2 |
| 8 | bayerite | 1.66 | 69.8 | 4.32 | 89.7 |
| 9 | active clay | 2.00 | 63.6 | 3.46 | 78.8 |
| 10 | diatomaceous earth | 2.20 | 60.0 | 3.34 | 80.7 |

EXAMPLE 11

To 45 ml of a 2 N aqueous solution of sodium hydroxide were added 6.20 g of 2-methoxyphenol, 14.25 g of a 20 wt % aqueous solution of glyoxylic acid and 2.50 g of aluminium oxide [manufactured by Kishida Chem. Co., Ltd., trade name: Kassei Alumina], and the mixture was subjected to reaction with stirring at 25° C. for 24 hours.

The aluminium oxide was separated from the reaction mixture by filtration and thus a reaction liquid was obtained. The aluminium oxide separated by filtration was washed with 20 ml of a 1 N aqueous solution of sodium hydroxide and the washing was added to the reaction liquid. The reaction liquid was adjusted to pH 6 by the addition of a 12 N hydrochloric acid and then the unaltered 2-methoxyphenol was extracted three times with 50 ml portions of diethyl ether. From the extract was recovered 2.10 g of 2-methoxyphenol.

In an autoclave were placed the remaining aqueous solution, 100 ml of a 1 N aqueous solution of sodium hydroxide and 0.55 g of copper (II) oxide and the mixture was subjected to reaction with stirring at 125° C. for 90 minutes under a pressure of 2 Kg/cm$^2$ (gauge) with introducing an air thereinto at a rate of 0.15 Nl/minute.

After 11 ml of a 12 N hydrochloric acid was added to the oxidation reaction mixture to adjust the pH value to 1.5, the mixture was extracted three times with 130 ml portions of diethyl ether. The extract was analyzed by gas chromatography. The results are shown in Table 3.

COMPARATIVE EXAMPLE 3

An experiment was run in the same manner as in Example 1 except that aluminium oxide was not used. After the first step, 2.10 g of 2-methoxyphenol was recovered.

The results are shown in Table 3. In the Tables shown hereinbelow, the yield was calculated based on the 2-alkoxyphenol consumed in the first step.

Table 3

| | 4-hydroxy-3-methoxy-benzaldehyde | | 2-hydroxy-3-methoxy-benzaldehyde | | 4-hydroxy-5-methoxy-isophthalaldehyde | |
|---|---|---|---|---|---|---|
| | yield | | yield | | yield | |
| | (g) | (%) | (g) | (%) | (g) | (%) |
| Example 11 | 4.63 | 92.1 | 0.29 | 5.8 | 0.06 | 1.0 |
| Comparative example 3 | 4.12 | 82.0 | 0.14 | 2.8 | 0.76 | 12.8 |

EXAMPLES 12–14

Experiments were run in the same manner as in Example 11 except that 0.10 g (Example 12), 0.50 g (Example 13) or 6.20 g (Example 14) of aluminium oxide was used. The recoveries of 2-methoxyphenol in the first step were 2.14 g, 2.08 g and 2.12 g in Examples 12–14, respectively.

The results are shown in Table 4.

COMPARATIVE EXAMPLE 4

An experiment was run in the same manner as in Example 11 except that 0.02 g of aluminium oxide was used. The amount of 2-methoxyphenol recovered after the first step was 2.16 g.

The results are shown in Table 4.

Table 4

|  | 4-hydroxy-3-methoxy-benzaldehyde yield | | 2-hydroxy-3-methoxy-benzaldehyde yield | | 4-hydroxy-5-methoxy-isophthalaldehyde yield | |
| --- | --- | --- | --- | --- | --- | --- |
|  | (g) | (%) | (g) | (%) | (g) | (%) |
| Example 12 | 4.21 | 84.6 | 0.20 | 4.0 | 0.42 | 7.1 |
| Example 13 | 4.51 | 89.3 | 0.26 | 5.1 | 0.15 | 2.5 |
| Example 14 | 4.58 | 91.6 | 0.29 | 5.8 | 0.06 | 1.0 |
| Comparative example 4 | 4.07 | 82.2 | 0.14 | 2.8 | 0.69 | 11.8 |

EXAMPLES 15–18

Experiments were run in the same manner as in Example 11 except that 3.00 g of respective hydrated aluminium oxides described in Table 5 was used in place of aluminium oxide.

The recoveries of 2-methoxyphenol after the first step and the results are shown in Table 5.

Table 5

|  | hydrated aluminum oxide | recovered 2-methoxy-phenol (g) | 4-hydroxy-3-methoxy-benzaldehyde yield | | 2-hydroxy-3-methoxy-benzaldehyde yield | | 4-hydroxy-5-methoxy-isophthal-aldehyde yield | |
| --- | --- | --- | --- | --- | --- | --- | --- | --- |
|  |  |  | (g) | (%) | (g) | (%) | (g) | (%) |
| Example 15 | gibbsite | 2.10 | 4.55 | 90.5 | 0.27 | 5.4 | 0.11 | 1.8 |
| Example 16 | bayrite | 2.07 | 4.61 | 91.1 | 0.28 | 5.5 | 0.08 | 1.3 |
| Example 17 | boehmite | 2.13 | 4.50 | 90.2 | 0.27 | 5.4 | 0.09 | 1.5 |
| Example 18 | diaspore | 2.18 | 4.48 | 90.9 | 0.28 | 5.7 | 0.07 | 1.2 |

EXAMPLE 19

An experiment was run in the same manner as in Example 11 except that 2.50 g of α-alumina (manufactured by Norton Co., Ltd., U.S.A.) was used for aluminium oxide.

The results are shown in Table 6. The recovery of 2-methoxyphenol after the first step was 2.13 g.

EXAMPLE 20

An experiment was run in the same manner as in Example 11 except that 2.50 g of silica-gel (manufactured by Fuji-Devisson Chem. Co., Ltd.) was used in place of aluminium oxide.

The results are shown in Table 6. The recovery of 2-methoxyphenol after the first step was 2.29 g.

Table 6

|  | 4-hydroxy-3-methoxy-benzaldehyde yield | | 2-hydroxy-3-methoxy-benzaldehyde yield | | 4-hydroxy-5-methoxy-isophthalaldehyde yield | |
| --- | --- | --- | --- | --- | --- | --- |
| Example | (g) | (%) | (g) | (%) | (g) | (%) |
| 19 | 4.56 | 91.4 | 0.30 | 6.0 | 0.07 | 1.2 |
| 20 | 4.25 | 88.7 | 0.25 | 5.2 | 0.20 | 3.5 |

EXAMPLES 21–23

Experiments were run in the same manner as in Example 11 except that each 2.50 g of silica-alumina manufactured by Gasukuro Kogyo Co., Ltd., Japan was used in place of aluminium oxide.

The ratios by weight of silica and alumina were 98:2, 60:40 and 10:90 in Examples 21–23, respectively. The recoveries of 2-methoxyphenol after the first step were 2.17 g, 2.27 g and 2.14 g in Examples 21–23, respectively.

The results are shown in Table 7.

Table 7

|  | 4-hydroxy-3-methoxy-benzaldehyde yield | | 2-hydroxy-3-methoxy-benzaldehyde yield | | 4-hydroxy-5-methoxy-isophthalaldehyde yield | |
| --- | --- | --- | --- | --- | --- | --- |
| Example | (g) | (%) | (g) | (%) | (g) | (%) |
| 21 | 4.36 | 88.3 | 0.25 | 5.1 | 0.19 | 3.2 |
| 22 | 4.20 | 87.2 | 0.23 | 4.8 | 0.23 | 4.0 |
| 23 | 4.46 | 89.6 | 0.27 | 5.4 | 0.13 | 2.2 |

EXAMPLES 24–25

Experiments were run in the same manner as in Example 11 except that each 2.50 g of the catalysts described in Table 8 was used in place of aluminium oxide. The recoveries of 2-methoxyphenol and the results are shown in Table 8.

Table 8

| Example | Catalyst | recovered 2-methoxy-phenol (g) | 4-hydroxy-3-methoxy-benzaldehyde yield | | 2-hydroxy-3-methoxy-benzaldehyde yield | | 4-hydroxy-5-methoxy-isophthal-aldehyde yield | |
| --- | --- | --- | --- | --- | --- | --- | --- | --- |
|  |  |  | (g) | (%) | (g) | (%) | (g) | (%) |
| 24 | diatomaceous earth | 2.41 | 4.15 | 89.3 | 0.26 | 5.6 | 0.10 | 1.8 |
| 25 | active clay | 2.30 | 4.24 | 88.7 | 0.25 | 5.2 | 0.18 | 3.2 |

EXAMPLE 26

An experiment was run in the same manner as in Example 11 except that 6.90 g of 2-ethoxyphenol was used in place of 2-methoxyphenol. The recovery of 2-ethoxyphenol after the first step was 2.30 g.
The results are shown in Table 9.

COMPARATIVE EXAMPLE 5

An experiment was run in the same manner as in Example 26 except that aluminium oxide was not used. The recovery of 2-ethoxyphenol after the first step was 2.34 g.
The results are shown in Table 9.

EXAMPLE 27

An experiment was run in the same manner as in Example 26 except that 2.50 g of silica-alumina (the ratio by weight of silica and alumina: 98:2) manufactured by Gasukuro Kogyo Co., Ltd., Japan was used in place of aluminium oxide. The recovery of 2-ethoxyphenol after the first step was 2.41 g.
The results are shown in Table 9.

EXAMPLE 28

An experiment was run in the same manner as in Example 26 except that 2.50 g of α-alumina (manufactured by Norton Co., Ltd., U.S.A.) was used for aluminium oxide. The recovery of 2-ethoxyphenol after the first step was 2.38 g.
The results are shown in Table 9.

EXAMPLE 29

An experiment was run in the same manner as in Example 26 except that 2.50 g of silica-gel manufactured by Wako Junyaku Kogyo Co., Ltd., Japan was used in place of aluminium oxide. The recovery of 2-ethoxyphenol after the first step was 2.33 g.
The results are shown in Table 9.

Table 9

| | 3-ethoxy-4-hydroxy-benzaldehyde yield | | 3-ethoxy-2-hydroxy-benzaldehyde yield | | 5-ethoxy-4-hydroxy-isophthal-aldehyde yield | |
|---|---|---|---|---|---|---|
| | (g) | (%) | (g) | (%) | (g) | (%) |
| Example 26 | 5.06 | 91.5 | 0.26 | 4.7 | 0.08 | 1.2 |
| Comparative example 5 | 4.75 | 86.6 | 0.25 | 4.6 | 0.33 | 5.1 |
| Example 27 | 4.80 | 88.9 | 0.27 | 5.0 | 0.15 | 2.4 |
| Example 28 | 4.94 | 90.9 | 0.28 | 5.2 | 0.11 | 1.7 |
| Example 29 | 4.91 | 89.3 | 0.30 | 5.5 | 0.11 | 1.7 |

EXAMPLES 30–33

Experiments were run in the same manner as in Example 26 except that each 3.00 g of the catalysts described in Table 10 was used in place of aluminium oxide. The recoveries of 2-ethoxyphenol and the results are shown in Table 10.

Table 10

| Example | catalyst | recovered 2-ethoxy-phenol (g) | 3-ethoxy-4-hydroxy-benzaldehyde yield | | 3-ethoxy-2-hydroxy-benzaldehyde yield | | 5-ethoxy-4-hydroxy-isophthal-aldehyde yield | |
|---|---|---|---|---|---|---|---|---|
| | | | (g) | (%) | (g) | (%) | (g) | (%) |
| 30 | gibbsite | 2.32 | 5.00 | 90.8 | 0.27 | 4.9 | 0.10 | 1.6 |
| 31 | bayerite | 2.29 | 5.01 | 90.3 | 0.28 | 5.0 | 0.08 | 1.2 |
| 32 | boehmite | 2.42 | 4.84 | 89.8 | 0.30 | 5.6 | 0.11 | 1.7 |
| 33 | diaspore | 2.40 | 4.84 | 89.4 | 0.28 | 5.2 | 0.11 | 1.7 |

What is claimed is:
1. An improved process for preparing protocatechualdehyde or a 3-alkoxy-4-hydroxybenzaldehyde represented by the formula

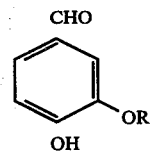

wherein R represents a methyl group or an ethyl group, which comprises reacting catechol or a 2-alkoxyphenol represented by the formula

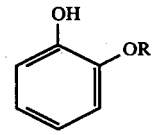

with glyoxylic acid in a basic aqueous medium to form a reaction product, and then oxidizing said reaction product in a basic aqueous medium,
the improvement comprising reacting said catechol or said 2-alkoxyphenol with glyoxylic acid in the range of 0.5–2 moles per mole of catechol or a 2-alkoxyphenol, in an aqueous medium containing a strong inorganic base and at least one catalyst selected from the group consisting of aluminum oxide, silicon oxide and hydrated aluminum oxide in an amount of not less than 0.01 g. per 1 g. of the starting catechol or 2-alkoxyphenol at a temperature of 0° to 50° C. to form said reaction product.
2. A process as claimed in claim 1 in which catechol is used.
3. A process as claimed in claim 1 in which 2-methoxyphenol is used.
4. A process as claimed in claim 1 in which 2-ethoxyphenol is used.
5. A process as claimed in claim 1, in which said strong inorganic base is sodium hydroxide, potassium hydroxide or sodium carbonate.
6. A process as claimed in claim 2 in which said strong inorganic base is sodium hydroxide, potassium hydroxide or sodium carbonate.
7. A process as claimed in claim 3, in which said strong inorganic base is sodium hydroxide, potassium hydroxide or sodium carbonate.
8. A process as claimed in claim 4, in which said strong inorganic base is sodium hydroxide, potassium hydroxide or sodium carbonate.